US009561356B2

(12) United States Patent
Cachemaille et al.

(10) Patent No.: US 9,561,356 B2
(45) Date of Patent: *Feb. 7, 2017

(54) MICRONEEDLE MANUFACTURING PROCESS WITH HATS

(71) Applicant: Debiotech S.A., Lausanne (CH)

(72) Inventors: Astrid Cachemaille, Bussigny (CH); François Cannehan, Lausanne (CH)

(73) Assignee: Debiotech S.A., Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/988,769

(22) Filed: Jan. 6, 2016

(65) Prior Publication Data

US 2016/0129232 A1 May 12, 2016

Related U.S. Application Data

(60) Continuation of application No. 13/507,368, filed on Jun. 22, 2012, now Pat. No. 9,266,718, which is a (Continued)

(30) Foreign Application Priority Data

Dec. 17, 2007 (EP) ..................... 07123416

(51) Int. Cl.
C25F 3/00 (2006.01)
B44C 1/22 (2006.01)
(Continued)

(52) U.S. Cl.
CPC ....... A61M 37/0015 (2013.01); B81C 1/00111 (2013.01); *A61M 2037/0053* (2013.01);
(Continued)

(58) Field of Classification Search
None
See application file for complete search history.

(56) References Cited

U.S. PATENT DOCUMENTS 5,683,546 A 11/1997 Manaka
7,258,805 B2 8/2007 Stemme et al.
(Continued)

FOREIGN PATENT DOCUMENTS

EP 597 302 5/1994
EP 1669100 6/2006
(Continued)

OTHER PUBLICATIONS

International Search Report (ISR) of PCT/IB2008/054280, May 13, 2009.
(Continued)

Primary Examiner — Allan Olsen
Assistant Examiner — Margaret D Klunk
(74) Attorney, Agent, or Firm — Andre Roland S.A.; Nikolaus Schibli

(57) ABSTRACT

Out-of-plane microneedle manufacturing process comprising the simultaneous creation of a network of microneedles and the creation of a polygonal shaped hat (2) above each microneedle (1) under formation, said process comprising the following steps: providing bridges (3) between the hats (3), maintaining the bridges (3) during the remaining microneedle manufacturing steps, removing the bridges (3), together with the hats (2), when the microneedles (1) are formed.

6 Claims, 11 Drawing Sheets

Related U.S. Application Data division of application No. 12/808,334, filed as application No. PCT/IB2008/054280 on Oct. 17, 2008, now Pat. No. 8,999,177.

(51) Int. Cl.
*C03C 15/00* (2006.01)
*A61M 37/00* (2006.01)
*B81C 1/00* (2006.01)

(52) U.S. Cl.
CPC ... *B81B 2201/055* (2013.01); *Y10T 29/49826* (2015.01); *Y10T 428/24479* (2015.01)

(56) References Cited

U.S. PATENT DOCUMENTS

| | | | |
|---|---|---|---|
| 8,999,177 B2* | 4/2015 | Cachemaille | 216/11 |
| 2008/0157427 A1 | 7/2008 | Chiou et al. | |

FOREIGN PATENT DOCUMENTS

| | | |
|---|---|---|
| JP | 2005-199392 | 7/2005 |
| WO | WO03/015860 | 2/2003 |
| WO | WO2008/003564 | 1/2008 |

OTHER PUBLICATIONS

Japanese Office Action of Dec. 18, 2012, and corresponding English translation, from counterpart Japanese Application 2010-538958.
Written Opinion of the International Searching Authority for PCT/IB2008/054280, May 13, 2009.
Griss et al., "Side-opened out-of-phane microneedles for microfluidic transdermal liquid transfer" J. Microelectromech. Sys., Jun. 25, 2003, vol. 12, No. 3, pp. 296-301.
Lang, "Silicon microstructuring technology," Materials Science and Engineering: R: Reports, vol. 17, Iss. 1, Sep. 1996, pp. 1-55.
Roxhed et al., "Penetration-enhanced ultrasharp microneedles and prediction on skin interaction for efficient transdermal drug delivery," J. Microelectromech. Sys., Dec. 6, 2007, vol. 16, No. 6, pp. 1429-1440.
Williams, Kirt R., Kishan Gupta, and Matthew Wasilik, "Etch rates for micromachining processing—Part II." Microelectromechanical Systems, Journal of 12.6 (2003): 761-778, p. 763.

* cited by examiner

FIGURE 2 (AA')

MICRONEEDLE MANUFACTURING PROCESS WITH HATS

This application is a continuation application of U.S. patent application Ser. No. 13/507,368, filed Jun. 22, 2013, 2013, which is a divisional application of U.S. patent application Ser. No. 12/808,334, filed Jun. 15, 2010, which is the U.S. national phase of the International Patent Application PCT/IB2008/054280, filed Oct. 17, 2008, which designated the U.S., and which claimed priority from European Application No. EP 07123416.5, filed Dec. 17, 2007, the entire contents of each of which are hereby incorporated by reference in this application.

FIELD OF INVENTION

The present invention relates to microneedles which are manufactured from a wafer, for instance a silicon wafer. The microneedles according to the invention may advantageously be used in the medical field, for intradermally administering a fluid in the body.

STATE OF THE ART

MEMS Microneedles may be classified in two groups, namely in-plane microneedles and out-of-plane microneedles. In the first group the microneedle shaft is parallel to the wafer while in the second group the shaft is perpendicular to the substrate. The out-of-plane microneedle group may itself be divided in two sub-groups, i.e. hollow microneedles and solid microneedles. The hollow microneedles have a through hole as described e.g. in patent applications WO 2002/017985 WO0217985 and WO 2003/015860. The microneedle manufacturing processes disclosed in the prior art use different designs and a combination of photolithography and etching (dry and/or wet etching) to obtain different microneedle shapes. A common feature in all those processes is the presence of a protective mask, generally made of silicon dioxide, above each microneedle under formation. This mask is commonly named "hat".

Some problems are however observed with the state-of-the-art microneedle manufacturing processes. For instance, in the manufacture of out-of-plane microneedles, the yield is limited by the difference of silicon etch rate between the centre and the border of the wafer. Because of this difference some microneedle hats (generally at the periphery of the wafer) fall before the end of the process. The consequence is that the microneedles underneath are no longer protected and as a consequence no longer etched in a controlled manner. Problems therefore arise, in particular microneedle malformation and low production yields.

GENERAL DESCRIPTION OF THE INVENTION

The problems discussed in the previous chapter are eliminated or at least notably reduced with the microneedle manufacturing process according to the invention which is characterized by the creation of bridges which link the hats between each others as well as between hats and edges during the manufacturing process.

More exactly the invention concerns an out-of-plane microneedle manufacturing process comprising the simultaneous creation of a network of microneedles and the creation of a polygonal shaped hat above each microneedle under formation, the process comprising the following steps:

providing bridges between the hats,
maintaining the bridges during the remaining microneedle manufacturing steps,
removing the bridges, together with the hats, when the microneedles are formed.

In the present text, the expression "polygonal hat" has to be understood" as a closed figure consisting of straight lines joined end to end.

A "polygonal hat" in the sense of the present text also include a circle. This object May be viewed as a polygone with straight lines tending towards zero.

Like the hats, the bridges are totally removed at the end of the manufacturing process and result in no modification of the microneedle design.

The bridges are preferably made of suspended structures.
They have a design which is compatible with the materials of the suspended structures and the microneedle fabrication process.

The bridges may have many different designs.
In one embodiment they are rectilinear.
In another embodiment they comprise a curved portion.
Advantageously, each bridge consists of a combination of rectilinear segments and of circle portions, e.g. of ½ and ¼ circles.

The bridge dimensions can vary depending on the distance between the microneedles as well as the distance between the microneedles and the edge of the wafer. The thickness of the bridges which is linked to the thickness of the hats can vary between 100 nm and 100 um: The width of the bridges can vary between 1 um and 100 um.

Moreover certain physical properties such as the mechanical resistance are affected by the size and shape of the bridges.

The material used must have the appropriate characteristics to support the manufacturing process. For example, for a process requiring an excellent conductivity, metal would be chosen.

Multilayered bridges, in particular with three layers, offer an interesting compromise when different properties are required as for example good conductivity, high selectivity and mechanical resistance to deformation.

DETAILED DESCRIPTION OF THE INVENTION

The invention is discussed below in a more detailed way with examples illustrated by the following figures.

NUMERICAL REFERENCES USED IN THE FIGURES

Figure 1:
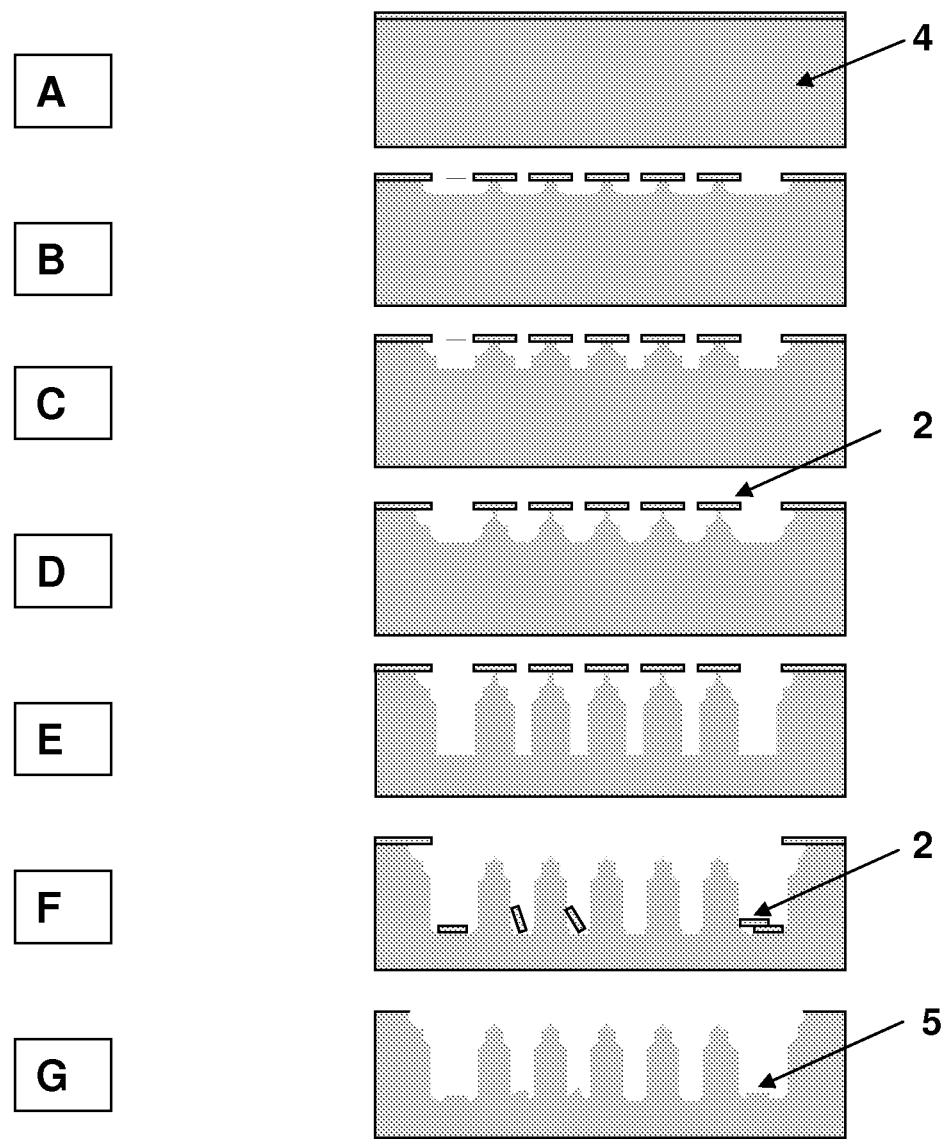
FIG. 1 shows a microneedle manufacturing process according to the state of the art.

1. Microneedle
2. Hat
3. Bridge
4. Wafer
5. Damaged area
6. Rectilinear segment
7. ½ circle
8. ¼ circle
9. Metal layer
10. SiO$_2$ layer State of the art MEMS microneedle fabrication process as described in FIG. 1 usually starts with a wafer, preferably a silicon wafer 4. On top of this silicon wafer a silicon dioxide layer is used as a protective mask to pattern the microneedles.

Figure 4:
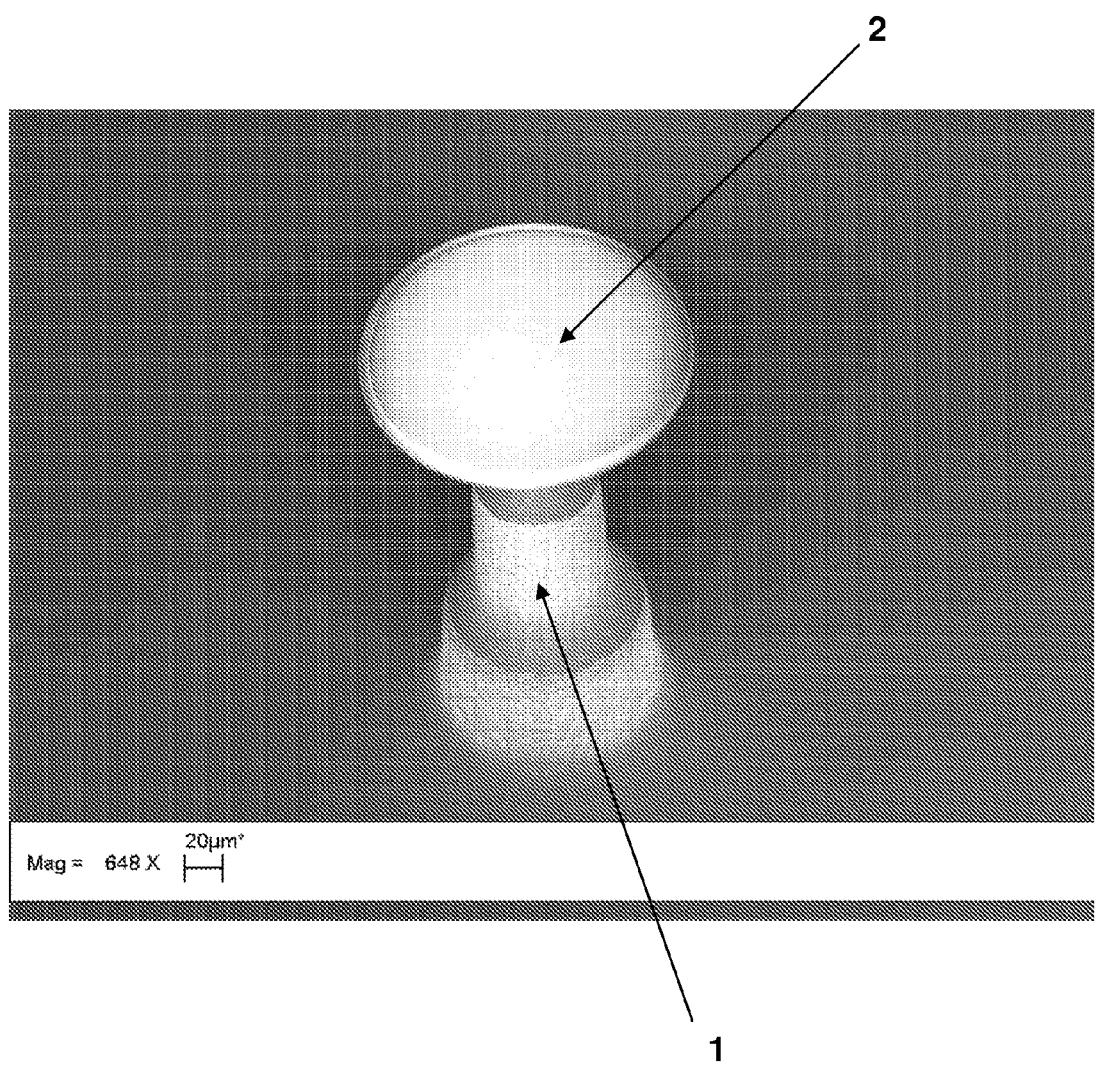
FIG. 4 is a picture of an assembly microneedle-hat according to the state of the art (without bridges)

This process aims at obtaining microneedles separated from each others and as a consequence the continuous protective mask in step A becomes discontinue at the start of the structuration of the microneedles step B. The parts of this discontinuous protective mask are called hats 2 and each microneedle is overlooked by a hat, protecting the microneedle and allowing controlled and well defined structuration. FIG. 4 shows an example of a microneedle creation 1 under a hat 2.

This structuration of the microneedles is performed by a sequence of isotropic and anisotropic etches as represented in FIG. 1 steps B to E.

The first isotropic etch as represented in FIG. 1 step B initiates the tip of the microneedle. The first anisotropic etch (FIG. 1, step C) is used to define the head of the microneedle.

The goal of the second isotropic etch as represented in FIG. 1 step D is to initiate the shoulder of the microneedle and to separate the head of the microneedle with the shaft which is obtain thanks to the second anisotropic etch (FIG. 1, step E). Finally comes the last isotropic etch (FIG. 1, step F) which is the most important etch of the process. Thanks to this etch, we pattern the tip of the microneedle, the backside trough holes and the final design of the microneedle, An oxidation and a silicon oxide etch as represented in FIG. 1, step G are then realized to remove the hats and to polish the silicon surface.

Frequently hats may fall before the end of the process (FIG. 1, step F, Ref. 2): This leads to a situation in which the structuration of the microneedle becomes uncontrolled resulting in malformation and low production yields. In addition the fallen hats provoke a bad surface state as shown in FIG. 1 Ref 5.

Figure 2:
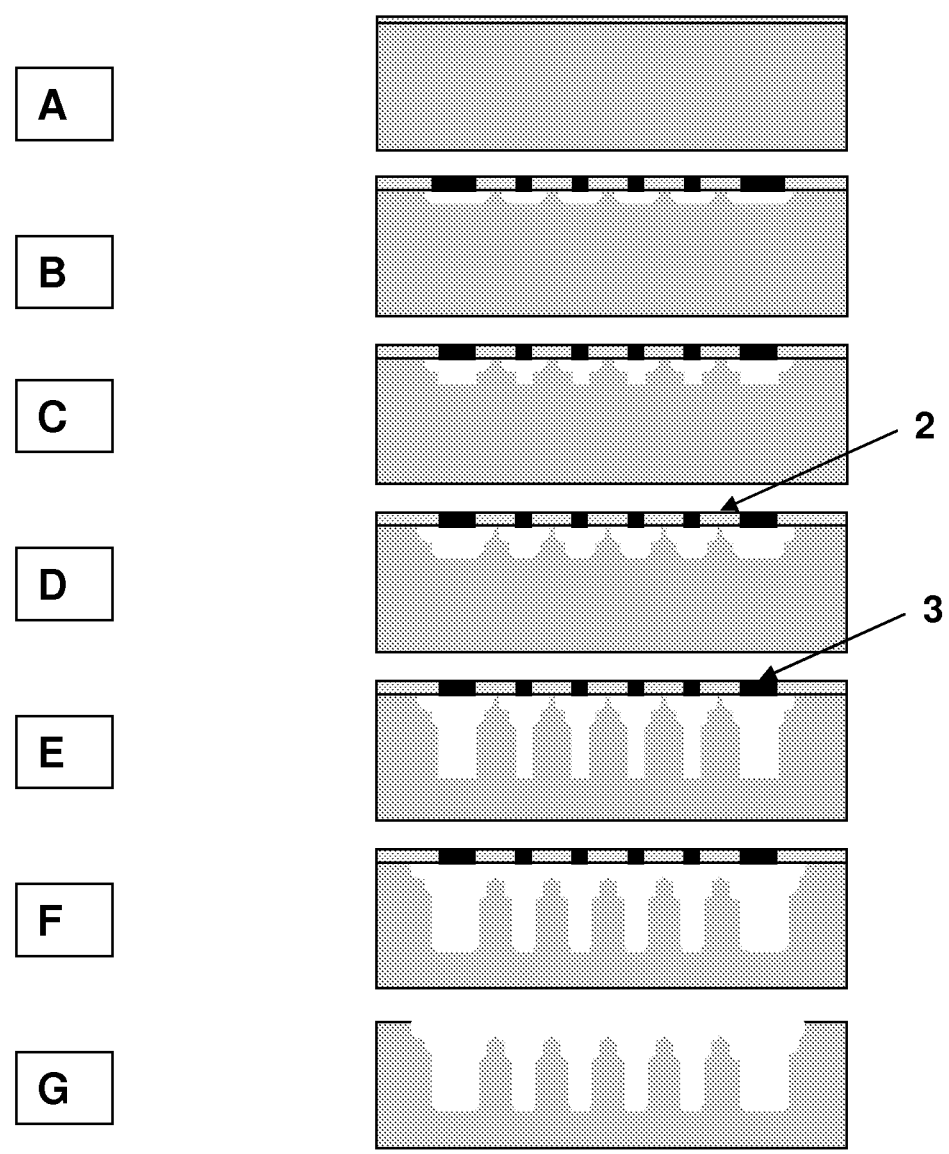
FIG. 2 shows a microneedle manufacturing process according to the invention.
Figure 3:
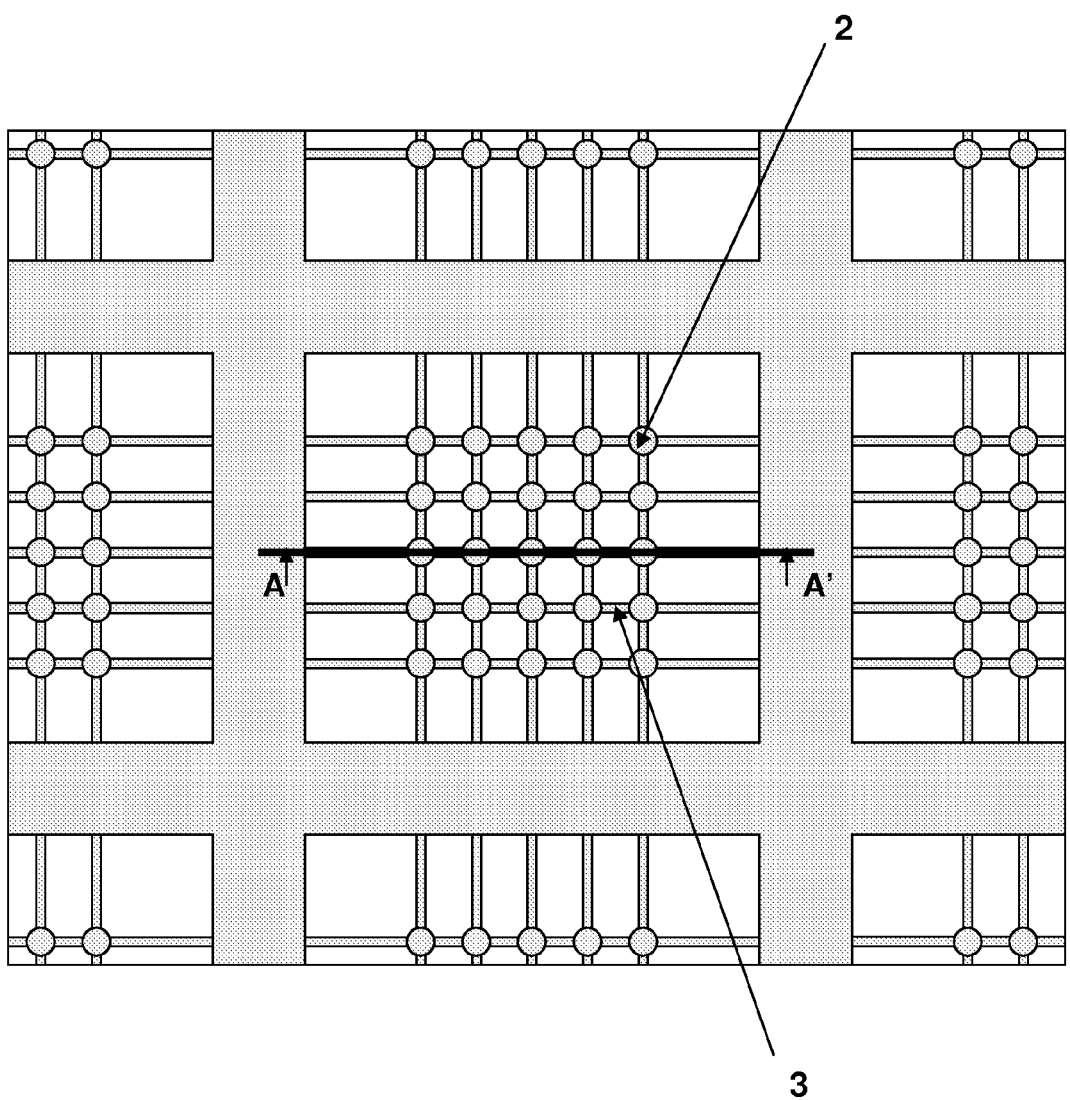
FIG. 3 is an upper view of the element shown in FIG. 2.
Figure 11:
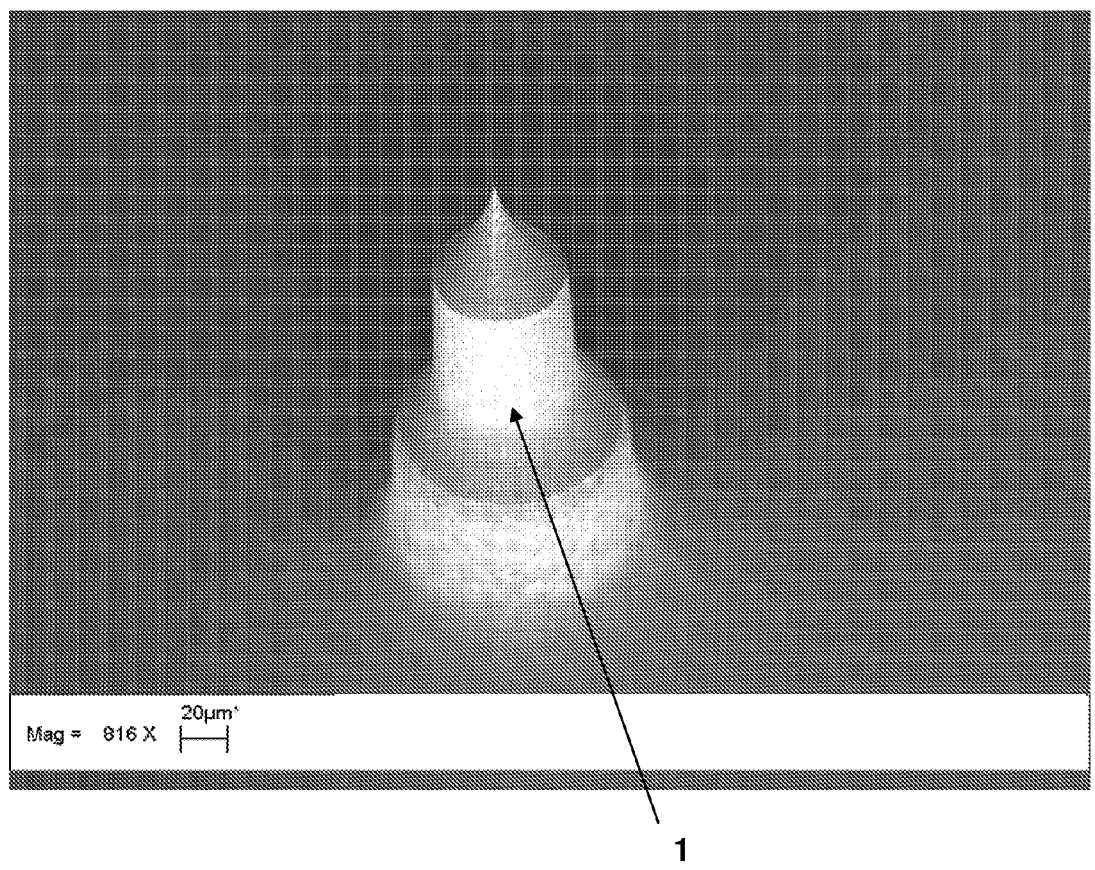
FIG. 11 is a picture of a microneedle obtained with a process according to the invention.

The present invention provides a way to hold the hats together so that they won't fall before the end of the process. To this effect the hats are linked together and are linked to the edges as displayed in FIG. 3. These links (FIG. 2, Ref 3), also named bridges in the present text, will stay in place up to the end of the process and guarantee the stability of each hat until the microneedle fabrication is ended (FIG. 2 Step F). When the process has been completed (FIG. 1 step G) the hat and their links are removed revealing perfect microneedles pattern (see e.g. FIG. 11) and chip surface state.

An important advantage of these links is that they do not modify the microneedle structuration parameters. The isotropic and anisotropic etches are the same with or without links.

As described earlier bridges and hats are deeply linked together; as a matter of fact their are made of same materials and have the same thickness.

Figure 5:
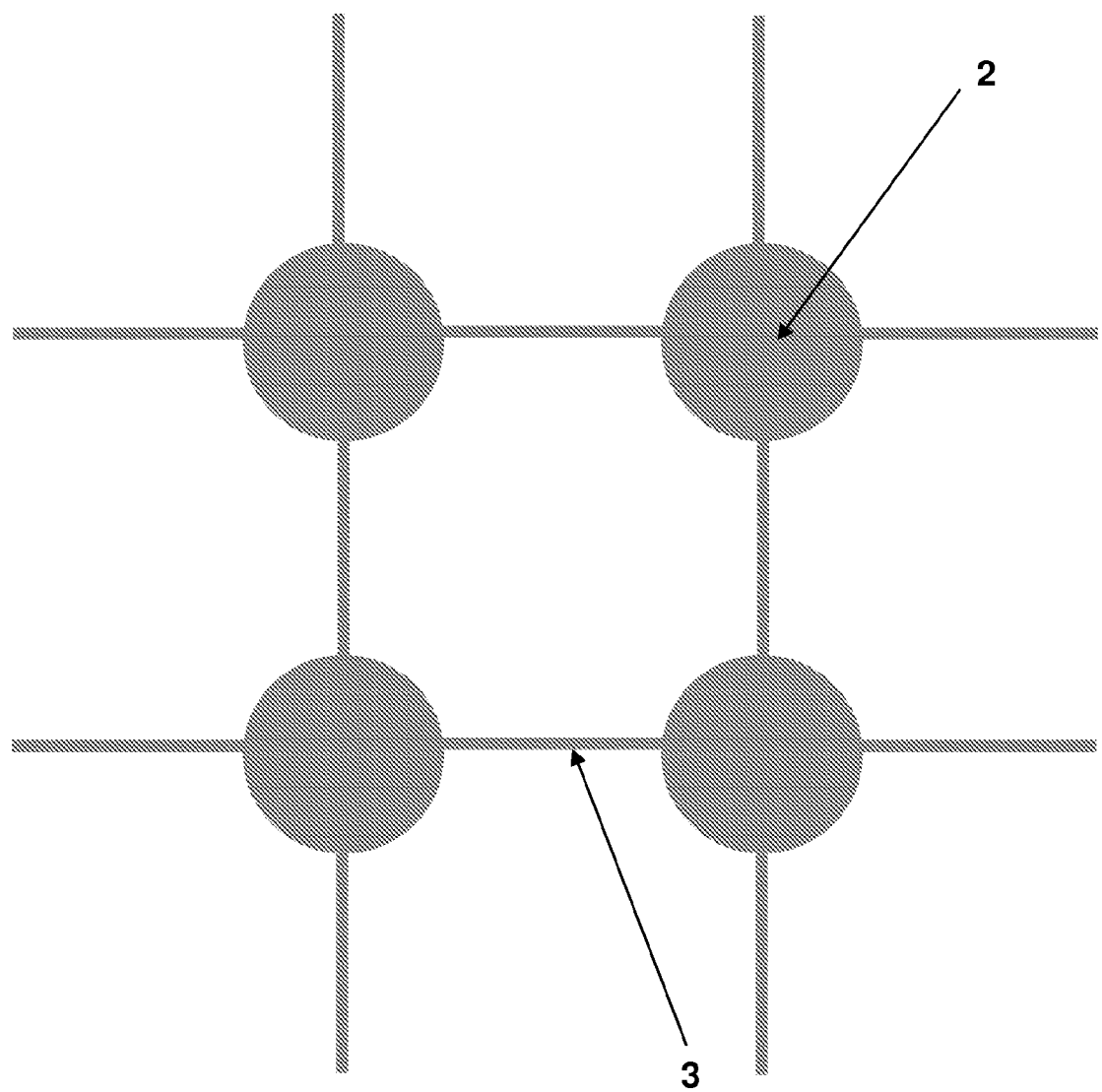
FIG. 5 shows one example of bridges according to the invention.
Figure 9:
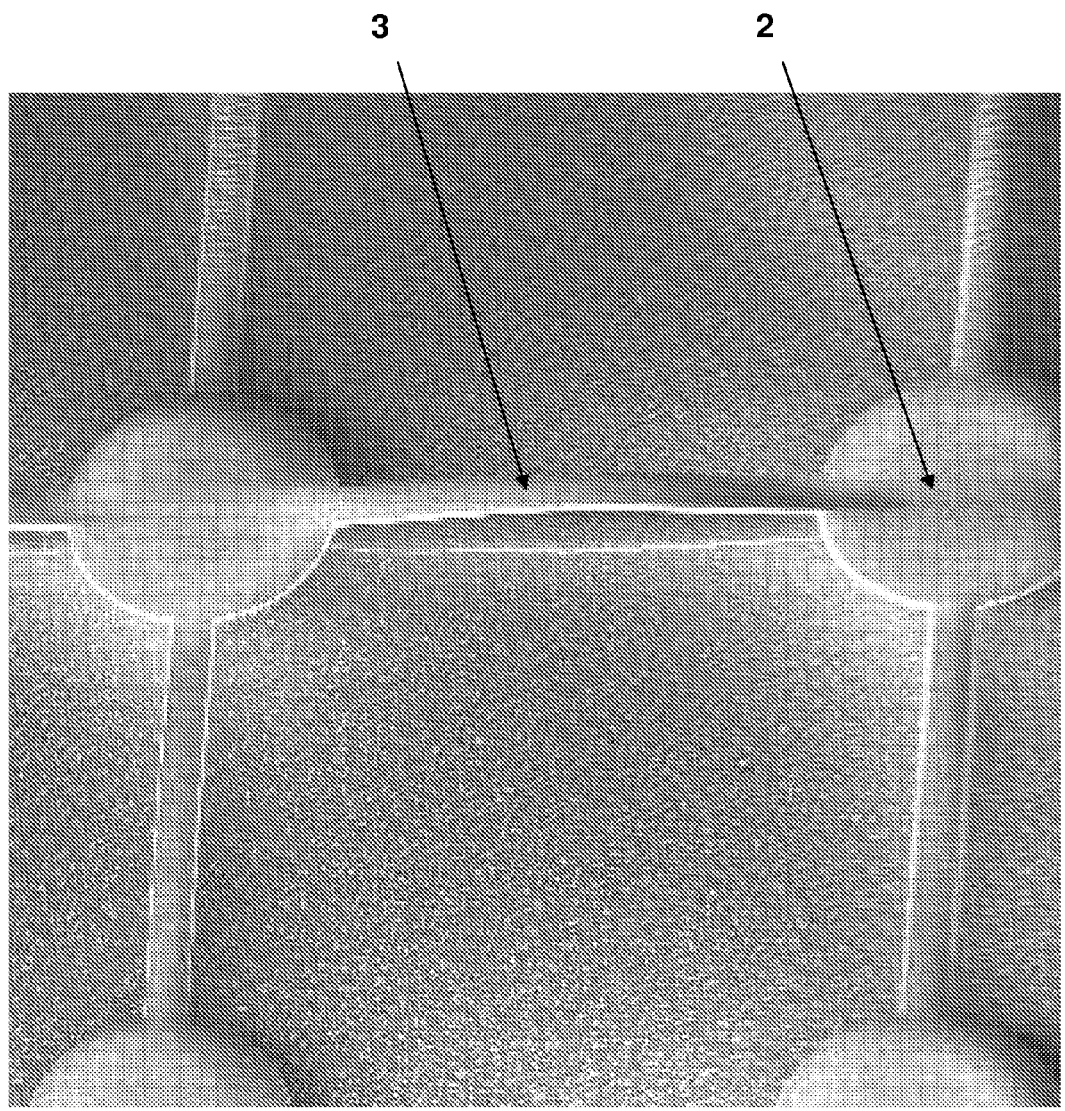
FIG. 9 is a picture of the example shown on FIG. 5.

As far as the design of the bridges is concerned it can take many forms. Simple linear bridge between the hats can be an option as shown schematically in FIG. 5 and on the picture in FIG. 9 which represents microneedle process of step B in FIG. 1.

Figure 6:
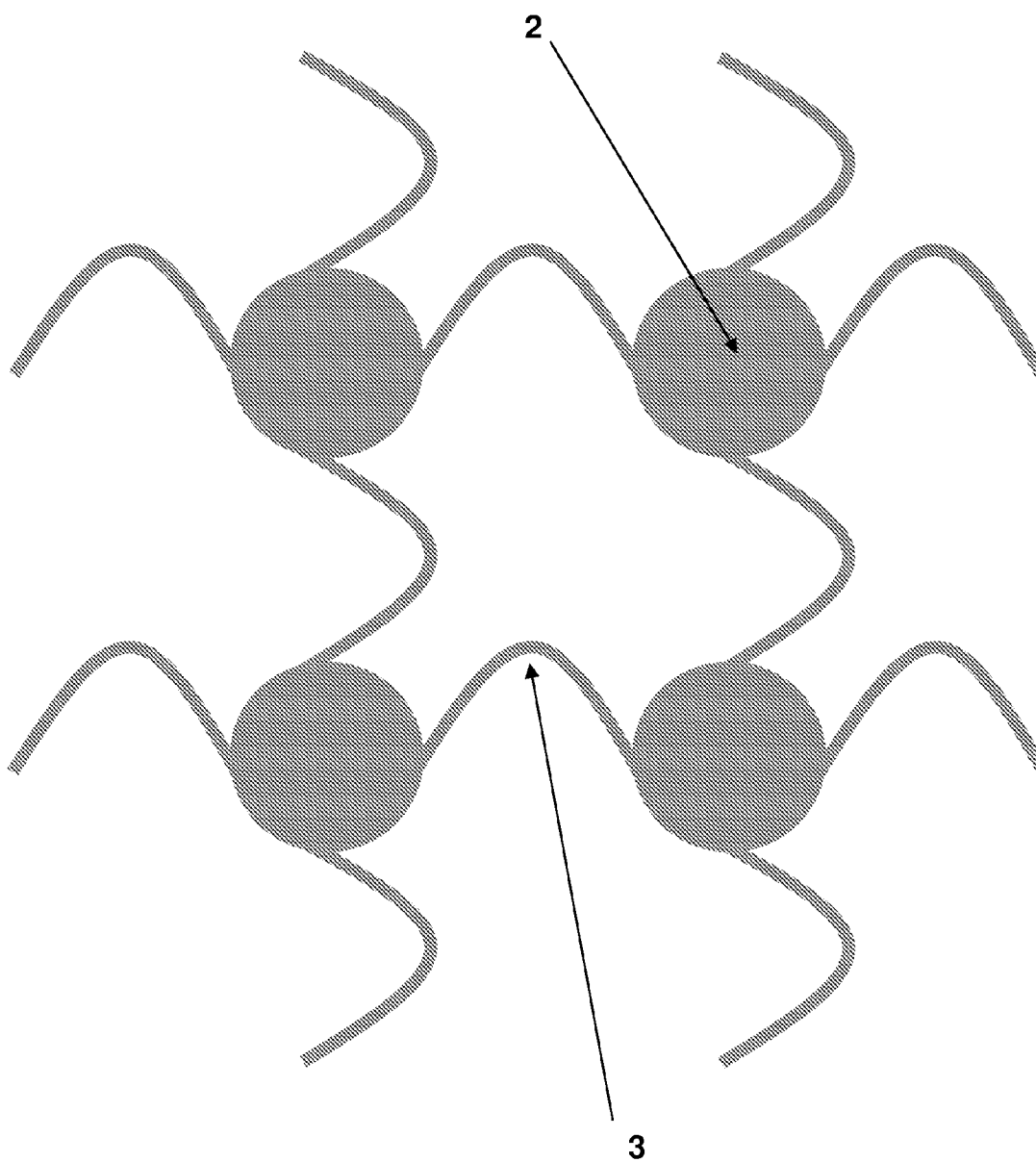
FIG. 6 shows another example of bridges according to the invention.
Figure 7:
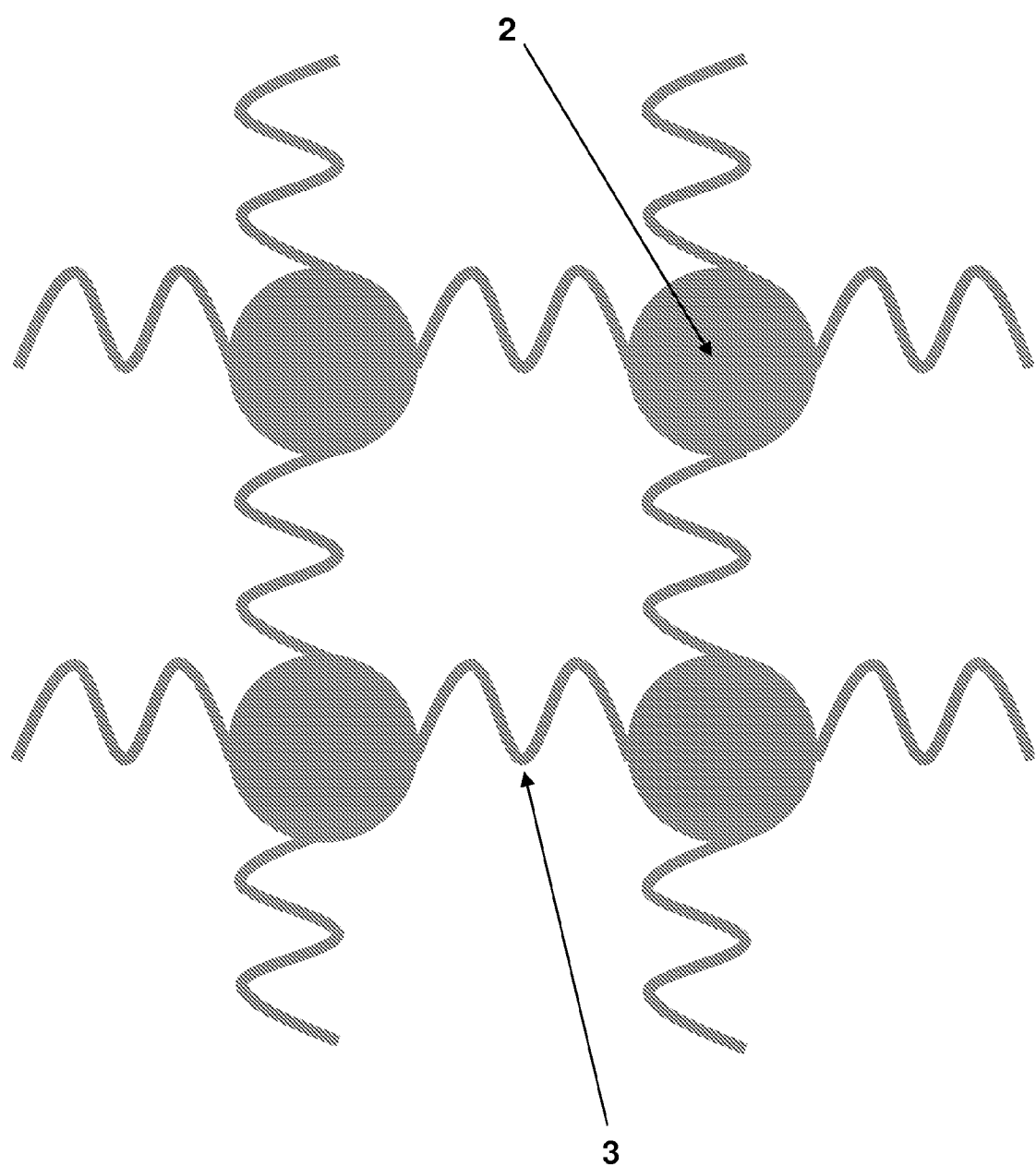
FIG. 7 shows another example of bridges according to the invention.
Figure 8:
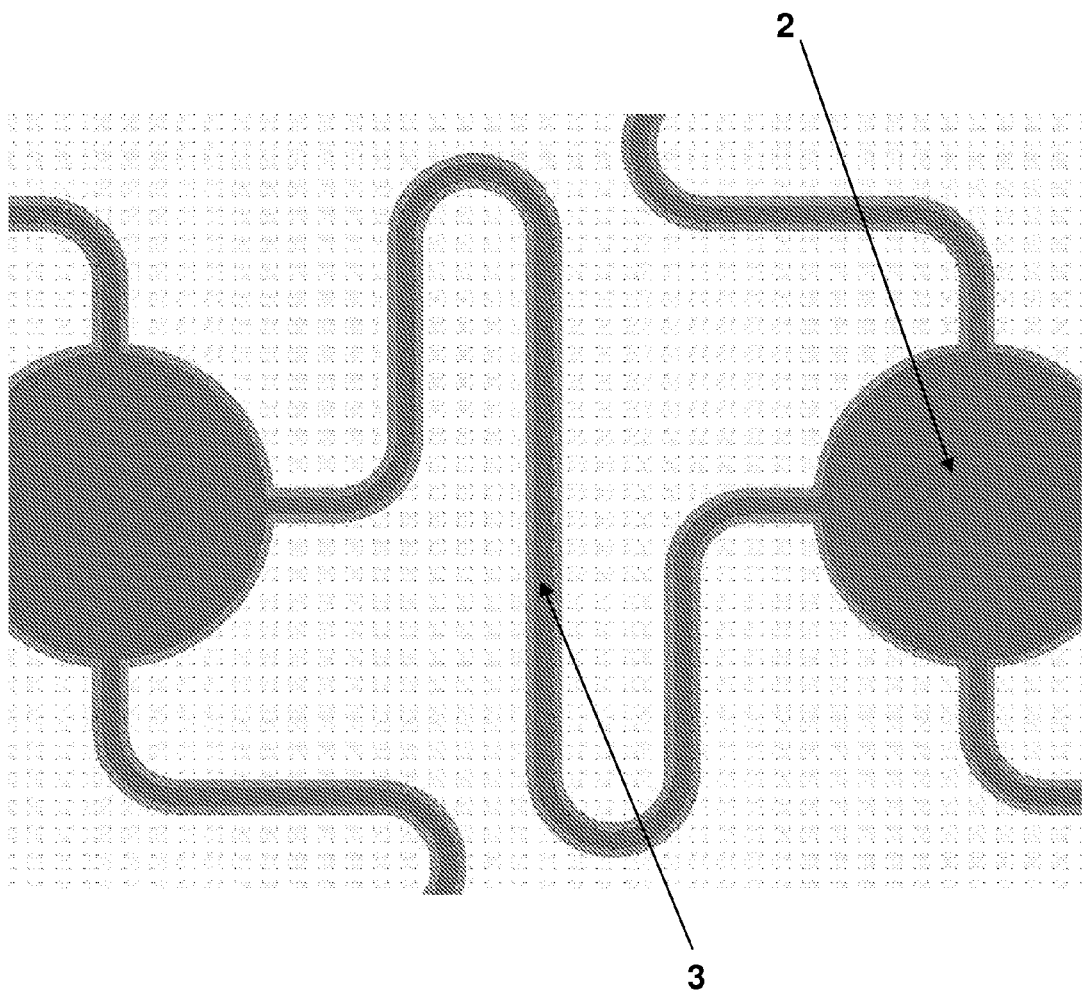
FIG. 8 shows another example of a bridges according to the invention.

Curved segments as in FIG. 6 and FIG. 7 or combination of rectilinear and curved segments as in FIG. 8 are also possible.

Figure 10:
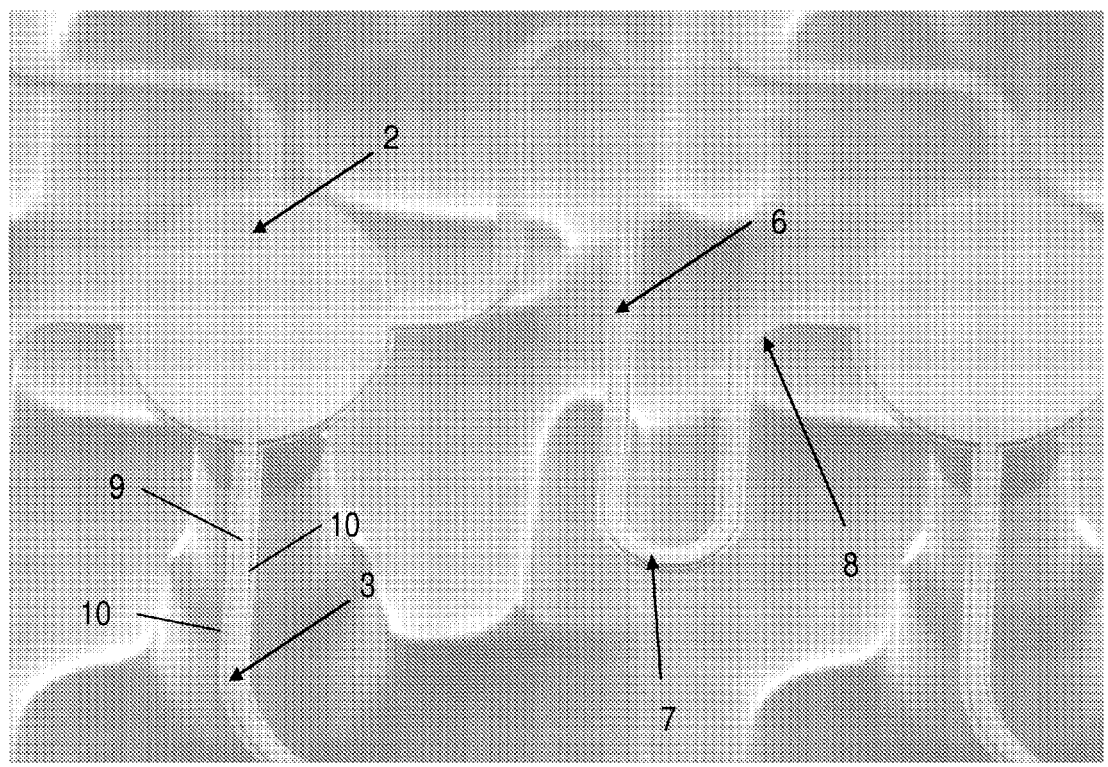
FIG. 10 is a picture of microneedles with hats and bridges before removal (status before FIG. 11)

Another aspect of the design of the bridges is the material. Single layer bridges can be appropriate for many processes but depending on the complexity of the process and also on the cleaning steps multilayer bridges can be a better option. Multilayered bridges improve the characteristics of the bridges (FIG. 10). We may associate metal layers (aluminium, tungsten, nickel . . . ) and no conductive layers (silicon dioxide, silicon nitride . . . ). The metal layers improve the thermal conductivity of the bridges and the non conductive layers improve the mechanical resistance and the high selectivity of the bridges.

The invention claimed is:

1. A method of manufacturing a microneedle comprising the steps of:
   (i) patterning a protective mask to form an etch opening in the protective mask for etching a wafer, the etch openings formed adjacent to an area of the wafer where the microneedle will be formed;
   (ii) first isotropic etching of an exposed area of the wafer at the etch opening to form a first cavity in the wafer;
   (iii) first anisotropic etching of the first cavity to define a head of the microneedle;
   (iv) second isotropic etching to form a shoulder of the microneedle, after the step (iii);
   (v) second anisotropic etching to form a shaft of the microneedle, after the step (iv);
   (vi) third isotropic etching to form a tip of the microneedle and to pattern a through hole, such that the tip of the microneedle detaches from the protective mask, after the step (v), and
   (vii) removing the protective mask after the step (vi).

2. The method of manufacturing the microneedle according to claim 1, wherein the step (vi) removes the wafer material along the entire shaft of the microneedle.

3. The method of manufacturing a microneedle according to claim 1, wherein the steps (ii), (iii), (iv), and (v) are configured such that they do not form a final shape of the tip of the microneedle.

4. The method of manufacturing a microneedle according to claim 1, wherein in the step (iv) of second isotropic etching, the tip of the microneedle does not detach from the hat of the protective mask.

5. The method of manufacturing a microneedle according to claim 1, wherein
   the step of (i) patterning the protective mask forms a plurality of etch openings in the protective mask, the plurality of etch openings formed adjacent to a hat and traversed by bridges formed by the protective mask.

6. The method of manufacturing a microneedle according to claim 5, wherein the bridges of the protective mask are multi-layered.

* * * * *